US008933023B2

(12) United States Patent
Pohl et al.

(10) Patent No.: US 8,933,023 B2
(45) Date of Patent: *Jan. 13, 2015

(54) RAPID ACTING INJECTABLE INSULIN COMPOSITIONS

(71) Applicant: Biodel Inc., Danbury, CT (US)

(72) Inventors: Roderike Pohl, Sherman, CT (US); Solomon S. Steiner, Mount Kisco, NY (US)

(73) Assignee: Biodel Inc., Danbury, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/156,307

(22) Filed: Jan. 15, 2014

(65) Prior Publication Data

US 2014/0135263 A1  May 15, 2014

Related U.S. Application Data

(63) Continuation of application No. 11/869,693, filed on Oct. 9, 2007, which is a continuation-in-part of application No. 11/077,604, filed on Mar. 11, 2005, now Pat. No. 7,279,457.

(60) Provisional application No. 60/609,194, filed on Sep. 9, 2004, provisional application No. 60/552,637, filed on Mar. 12, 2004.

(51) Int. Cl.
*A61K 38/28* (2006.01)
*A61K 47/18* (2006.01)
*A61K 9/00* (2006.01)
*A61K 47/12* (2006.01)

(52) U.S. Cl.
CPC ............. *A61K 47/183* (2013.01); *A61K 9/0056* (2013.01); *A61K 38/28* (2013.01); *A61K 47/12* (2013.01)
USPC ......................................................... 514/5.9

(58) Field of Classification Search
None
See application file for complete search history.

(56) References Cited

U.S. PATENT DOCUMENTS

| | | |
|---|---|---|
| 2,143,590 A | 1/1939 | Scott |
| 2,626,228 A | 1/1953 | Petersen |
| 2,819,999 A | 1/1958 | Schlichtkrull |
| 3,649,456 A | 3/1972 | De Benneville et al. |
| 3,683,635 A | 8/1972 | Campanelli |
| 3,906,950 A | 9/1975 | Cocozza |
| 3,921,637 A | 11/1975 | Bennie et al. |
| 4,129,560 A | 12/1978 | Zoltobrocki |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,343,898 A | 8/1982 | Markussen |
| 4,364,385 A | 12/1982 | Lossef |
| 4,377,482 A | 3/1983 | Rivier |
| 4,459,226 A | 7/1984 | Grimes |
| 4,489,159 A | 12/1984 | Markussen |
| 4,511,505 A | 4/1985 | Morihara |
| 4,659,696 A | 4/1987 | Hirai |
| 4,861,627 A | 8/1989 | Mathiowitz |
| 4,866,051 A | 9/1989 | Hunt |
| 4,946,828 A | 8/1990 | Markussen |
| 5,006,343 A | 4/1991 | Benson |
| 5,042,975 A | 8/1991 | Chien |
| 5,045,454 A | 9/1991 | Bertheussen |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,329,976 A | 7/1994 | Haber |
| 5,352,461 A | 10/1994 | Feldstein et al. |
| 5,354,562 A | 10/1994 | Platz |
| 5,364,838 A | 11/1994 | Rubsamen |
| 5,442,043 A | 8/1995 | Fukuta et al. |

(Continued)

FOREIGN PATENT DOCUMENTS

| | | |
|---|---|---|
| AU | 7905194 | 6/1995 |
| CA | 2 136 704 | 5/1995 |

(Continued)

OTHER PUBLICATIONS

U.S. Appl. No. 12/324,717, filed Nov. 28, 2008, Steiner, et al.
"Human Insulin", GenBank Accession No. AAA59172, pp. 1-2, accessed Feb. 17, 2009.
"Bovine Insulin", GenBank Accession No. ACD35246, pp. 1-2, accessed Feb. 17, 2009.
"Types of Insulin", http://www.diabetes.org/for-parents-and-kids/diabetes-care/types-actions.jsp, pp. 1-2, accessed Feb. 17, 2009.
U.S. Appl. No. 12/397,219, filed Mar. 3, 2009, Steiner, et al.
US 5,785,981, 07/1998, Stanley, et al. (withdrawn).
Culy, et al., "Management of diabetes mellitus: Defining the role of insulin lispro mix 75/25", Dis. Man. Health. Outcome, 9(12): 711-730 (2001).

(Continued)

*Primary Examiner* — Christina Bradley
(74) *Attorney, Agent, or Firm* — Pabst Patent Group LLP (57) ABSTRACT

Injectable insulin formulations with improved stability and rapid onset of action are described herein. The formulations may be for subcutaneous, intradermal or intramuscular administration. In the preferred embodiment, the formulations are administered via subcutaneous injection. The formulations contain insulin in combination with a chelator and dissolution agent, and optionally additional excipients. In the preferred embodiment, the formulation contains human insulin, a zinc chelator such as EDTA and a dissolution agent such as citric acid. These formulations are rapidly absorbed into the blood stream when administered by subcutaneous injection. In the preferred embodiment, the insulin is provided as a dry powder in a sterile vial. This is mixed with a diluent containing a pharmaceutically acceptable carrier, such as water, a zinc chelator such as EDTA and a dissolution agent such as citric acid shortly before or at the time of administration. In another embodiment, the insulin is stored as a frozen mixture, ready for use upon thawing.

14 Claims, 5 Drawing Sheets

(56) References Cited

U.S. PATENT DOCUMENTS

| | | |
|---|---|---|
| 5,458,135 A | 10/1995 | Patton et al. |
| 5,474,978 A | 12/1995 | Bakaysa |
| 5,482,927 A | 1/1996 | Maniar |
| 5,484,606 A | 1/1996 | Dhabar et al. |
| 5,492,112 A | 2/1996 | Mecikalski et al. |
| 5,503,852 A | 4/1996 | Steiner et al. |
| 5,514,646 A | 5/1996 | Chance et al. |
| 5,534,488 A | 7/1996 | Hoffmann |
| 5,547,929 A | 8/1996 | Anderson, Jr. et al. |
| 5,562,909 A | 10/1996 | Allcock et al. |
| 5,577,497 A | 11/1996 | Mecikalski et al. |
| 5,650,486 A | 7/1997 | De Felippis |
| 5,653,961 A | 8/1997 | McNally et al. |
| 5,653,987 A | 8/1997 | Modi et al. |
| 5,658,878 A | 8/1997 | Bäckström et al. |
| 5,672,359 A | 9/1997 | Digenis |
| 5,693,338 A | 12/1997 | Milstein |
| 5,731,291 A | 3/1998 | Sullivan et al. |
| 5,740,794 A | 4/1998 | Smith et al. |
| 5,747,445 A | 5/1998 | Bäckström et al. |
| 5,763,396 A | 6/1998 | Weiner et al. |
| RE35,862 E | 7/1998 | Steiner et al. |
| 5,783,556 A | 7/1998 | Clark |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,898,028 A | 4/1999 | Jensen |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,132,766 A | 10/2000 | Sankaram |
| 6,153,613 A | 11/2000 | Ono et al. |
| RE37,053 E | 2/2001 | Hanes et al. |
| 6,254,854 B1 | 7/2001 | Edwards et al. |
| 6,264,981 B1 | 7/2001 | Zhang |
| 6,294,204 B1 | 9/2001 | Rossling et al. |
| 6,310,038 B1 | 10/2001 | Havelund |
| 6,331,318 B1 | 12/2001 | Milstein |
| 6,395,744 B1 | 5/2002 | Adams et al. |
| 6,395,774 B1 | 5/2002 | Milstein |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,444,226 B1 | 9/2002 | Steiner et al. |
| 6,447,753 B2 | 9/2002 | Edwards et al. |
| 6,465,425 B1 | 10/2002 | Tracy |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger, III |
| 6,685,967 B1 | 2/2004 | Patton |
| 6,737,045 B2 | 5/2004 | Patton |
| 6,949,258 B2 | 9/2005 | Zhang |
| 6,960,561 B2 | 11/2005 | Boderke |
| 7,030,084 B2 | 4/2006 | Ekwuribe et al. |
| 7,089,934 B2 | 8/2006 | Staniforth et al. |
| 7,192,919 B2 | 3/2007 | Tzannis |
| 7,279,457 B2 | 10/2007 | Pohl et al. |
| 2001/0039260 A1 | 11/2001 | Havelund |
| 2001/0043934 A1 | 11/2001 | L'Italien et al. |
| 2002/0028767 A1 | 3/2002 | Jensen |
| 2002/0198140 A1 | 12/2002 | Havelund |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0143195 A1 | 7/2003 | Pinsker |
| 2003/0172924 A1 | 9/2003 | Staniforth et al. |
| 2003/0194420 A1 | 10/2003 | Holl et al. |
| 2004/0077528 A1 | 4/2004 | Steiner |
| 2004/0096403 A1 | 5/2004 | Steiner |
| 2004/0151774 A1 | 8/2004 | Pauletti et al. |
| 2004/0157928 A1 | 8/2004 | Kim et al. |
| 2004/0182387 A1 | 9/2004 | Steiner |
| 2004/0247628 A1 | 12/2004 | Lintz et al. |
| 2005/0080000 A1 | 4/2005 | Thurow et al. |
| 2005/0153874 A1 | 7/2005 | Cheatham |
| 2005/0203001 A1 | 9/2005 | Arbit |
| 2005/0214251 A1 | 9/2005 | Pohl |
| 2006/0067891 A1 | 3/2006 | Modi |
| 2007/0086952 A1 | 4/2007 | Steiner |
| 2007/0134279 A1 | 6/2007 | Stern |
| 2007/0155654 A1 | 7/2007 | Langkjaer |
| 2007/0235365 A1 | 10/2007 | Pohl et al. |
| 2008/0039365 A1 | 2/2008 | Steiner et al. |
| 2008/0039368 A1 | 2/2008 | Steriner et al. |
| 2008/0085298 A1 | 4/2008 | Pohl et al. |
| 2008/0096800 A1 | 4/2008 | Pohl et al. |
| 2009/0215669 A1 | 8/2009 | Myers |

FOREIGN PATENT DOCUMENTS

| | | |
|---|---|---|
| DE | 247684 | 7/1987 |
| EP | 0/069/715 | 1/1983 |
| EP | 0/122/036 | 10/1984 |
| EP | 0 220 958 A2 | 5/1987 |
| EP | 0/237/507 | 9/1987 |
| EP | 0 257 915 | 2/1988 |
| EP | 0/360/340 | 3/1990 |
| EP | 0/364/235 | 4/1990 |
| EP | 0/606/486 | 12/1993 |
| EP | 0655237 | 5/1995 |
| EP | 0 655 237 | 3/1996 |
| EP | 0748213 | 12/1996 |
| EP | 1/114/644 | 7/2001 |
| EP | 1 428 524 | 6/2004 |
| EP | 96911738 | 6/2004 |
| GB | 2 069 502 | 8/1981 |
| GB | 2240337 | 7/1991 |
| JP | 0149545 | 2/1992 |
| JP | 63020301 A | 1/1998 |
| WO | WO 90/13285 | 11/1990 |
| WO | WO 91/04011 | 4/1991 |
| WO | WO 91/08764 | 6/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | WO 93/17728 | 9/1993 |
| WO | WO 93/18754 | 9/1993 |
| WO | WO 94/00291 | 1/1994 |
| WO | WO 95/00127 | 1/1995 |
| WO | WO 95/11666 | 5/1995 |
| WO | WO 95/31979 | 11/1995 |
| WO | WO 95/34294 | 12/1995 |
| WO | WO 96/10996 | 4/1996 |
| WO | WO 96/36314 | 11/1996 |
| WO | WO 96/36352 | 11/1996 |
| WO | WO 97/33531 | 9/1997 |
| WO | WO 97/49386 | 12/1997 |
| WO | WO 98/42367 | 10/1998 |
| WO | WO 98/42368 | 10/1998 |
| WO | WO 98/42749 | 10/1998 |
| WO | WO 99/52506 | 10/1999 |
| WO | WO 01/00654 | 1/2001 |
| WO | WO 01/07107 | 2/2001 |
| WO | WO 02/11676 | 2/2002 |
| WO | WO 03/057170 | 7/2003 |

(56) References Cited

FOREIGN PATENT DOCUMENTS

| WO | WO 03/086345 | 10/2003 |
|---|---|---|
| WO | WO 03/094951 | 11/2003 |
| WO | WO 2004/056314 | 7/2004 |
| WO | WO 2004/075919 | 9/2004 |
| WO | WO 2004/080401 | 9/2004 |
| WO | WO 2005/089722 | 9/2005 |
| WO | WO 2006/088473 | 8/2006 |
| WO | WO 2007/041481 | 4/2007 |
| WO | WO 2007/047948 | 4/2007 |
| WO | WO 2007/121256 | 10/2007 |

OTHER PUBLICATIONS

Edelman, et al., "A double-blinded placebo-controlled trial assessing pramlintide treatment in the setting of intensive insulin therapy in type 1 diabetes", *Diabetes Care*, 29(10):2189-2195 (2006).

HUMALOG®, Mix 75/25TM "Patient Information", Eli Lilly, pp. 1-4, accessed Jun. 18, 2009.

Karl, et al., Pramlintide as an adjunct to insulin in patients with type 2 diabetes in a clinical practice setting reduced AIC, postprandial glucose excursions, and weight, *Diabetes Technology and Therapeutics*, 9(2):191-199 (2007).

Lalli, et al., "Long-term intensive treatment of type 1 diabetes with the short-acting insulin analog lispro in variable combination with NPH insulin at mealtime", *Diabetes Care*, 22(3):468-77 (1999).

Molitch, et al., "How long should insulin be used once a vial is started?", *Diabetes Care*, 27(5):1240-1; author reply 1241-2 (2004).

Moren, "Aerosol dosage forms and formulations" in *Aerosols in Medicine*, (2nd ed.), Elsevier, pp. 321-350 (1993).

Nilsson, et al., "Low levels of asparagine deamidation can have a dramatic effect on aggregation of amyloidogenic peptides: implications for the study of amyloid formation", *Protein Science*, 11(2): 342-349 (2002).

Plum, et al., "Pharmacokinetics of the rapid-acting insulin analog, insulin aspart, in rats, dogs, and pigs, and pharmacodynamics of insulin aspart in pigs.", *Drug Metab. Dispos.*, 28(2):155-60 (2000).

Roach, et al., "Improved postprandial glycemic control during treatment with Humalog Mix25, a novel protamine-based insulin lispro formulation. Humalog Mix25 Study Group", *Diabetes Care*, 22(8):1258-61 (1999).

Becker, "Insulin glulisine complementing basal insulins: A review of structure and activity", Diabetes Tech and Therp., 9(1):109-21 (2007).

Gaetani, et al., "Catalase and glutathione peroxidase are equally active in detoxification of hydrogen peroxide in human erythrocytes", Blood Journal, 73 (1):334-339 (1989).

Gerich, "Insulin glargine: long-acting basal insulin analog for improved metabolic control", Curr. Med. Res. & Opin., 20(1):31-37 (2004).

Rungby, et al., "New strategies in insulin treatment: analogues and noninvasive routes of administration", Fundamental & Clinical Pharm., 19:127-32 (2004).

U.S. Appl. No. 12/348,839, filed Jan. 5, 2009, Kashyap, et al.

"FDA Approves Rapid-acting insulin ApidraB from treatment of children with diabetes", http://www.medicalnewstoday.com/articles/ I27409.php, pp. 1-6 (2008). Accessed Apr. 30, 2009.

Actrapid, "Summary of product characteristics", http://emc.medicines.org.uk/medicine/3513/SPC/ Actrapid+100+IU+ml,+Solution+for+Injection+in+a+vial/, pp. 1-6; revised (2007); (accessed Apr. 20, 2009).

Insulin from Diabetes Forecast, 2008 *Resource Guide*, RGI 1-RG14. (2008).

Kashyap, "Design and evaluation of biodegradable, biosensitive in situ gelling system for pulsatile delivery of insulin" *Biomaterials*, 28(11):2051-60 (2007). Epub Jan. 19, 2007.

Lantus, "Lantus prescribing information-Aventis Pharmaceuticals", http://products.sanofi-aventis.us/lantus/lantus.html, pp. 1-45. Accessed Apr. 30, 2009.

Levemir from www.levemir.com, pp. 1-15 (2007). Accessed Apr. 30, 2009.

Talrose, et al., "Radiation resistivity of frozen insulin solutions and suspensions", *Int. J. Appl. Radiat. Isot.*, 32(10):753-6 (1981).

Traitel, et al., "Characterization of glucose-sensitive insulin release systems in simulated in vivo conditions", *Biomaterials*, 21(16):1679-87 (2000).

Velosulin, "Information for health professionals, Production Data Sheet", http://www.medsafe.gov.nz/profs/datasheet/v/VelosulinMCinj.htm, pp. 1-5; (2000); (accessed Apr. 20, 2009).

Zhang, et al., "Modulated insulin permeation across a glucose-sensitive polymeric composite membrane", *J. Control Release*, 80(1-3):169-78 (2002).

Ghilzai, "New developments in insulin delivery", Drug Dev Ind Pharm., 29(3):253-65 (2003).

Aungst & Rogers, "Site dependence of absorption-promoting actions of laureth-9, Na salicylate, Na2EDTA, and aprotinin on rectal, nasal, and buccal insulin delivery", *Pharm. Res.*, 5(5):305-308 (1988).

Brange, et al., Chemical stability of insulin 1: hydrolytic degradation during storage of pharmaceutical preparations, *Pharm. Res.*, 9:715-726 (1992).

De Sousa, et al., "Biocompatibility of EDTA, EGTA and citric acid", *Braz. Dent. J.*, 16:3-8 (2005).

Kang, et al., "Subcutaneous insulin absorption explained by insulin's physiochemical properties", *Diabetes Care*, 14:942-948 (1991).

Keowmaneechai, et al., "Influence of EDTA and citrate on physiochemical properties of whey protein-stabilized oil-in-water emulsions containing $CaCl_2$", *J. Agricultural and Food, Chemistry*, 50:7145-7153 (2002).

Klauser, et al., "Mixtures of human intermediate and human regular insulin in type 1 diabetic patients", *Diabetes Res. and Clin. Practice*, 5:185-190 (1988).

Monch & Dehnen, "High-performance liquid chromatography of polypeptides and proteins on a reversed-phase support", *Journal of Chromatography*, 147:415-418 (1978).

Quinn, et al., "Minimizing the aggregation of insulin solutions", *J. Pharmaceutical Sci.*, 72:1472-1473 (1983).

Szepesy & Horvath, "Specific salt effects in hydrophobic interaction chromatography of proteins", *Chromatographia*, 26:13-18 (1988).

Todo, et al., "Effect of additives on insulin absorption from intracheally administered dry powders in rats", *Int. J. Pharmaceutics*, 220:101-110 (2001).

Davidson, et al.,"Effect of premixed nph and regular insulin on glucose control and health-related quality of life in patients with type 2 diabetes mellitus", *Endocrine Practice*, 3(6):331-336 (1997).

Bauer, et al.,"Assessment of beta-adrenergic receptor blockade after isamoltane, a 5-HT1-receptor active compound, in healthy volunteers," *Clin. Pharmacol Ther* 53:76-83 (1993).

Benita, "Characterization of Drug-Loaded Poly(d,I-lactide) Microspheres," *J. Pharm. Sci.*,73: 1721-1724 (1984).

Bensch, et al., "Absorption of intact protein molecules across the pulmonary air-tissue barrier," *Science* 156: 1204-1206 (1967).

Brange, et al., "Insulin Structure and stability", *Pharm Biotechnol.*, 5:315-50 (1993).

Cerasi, et al., "Decreased sensitivity of the pancreatic beta cells to glucose in prediabetic and diabetic subjects. A glucose dose-response study," *Diabetes* 21(4): 224-34 (1972).

Cefalu, et al, "Inhaled Human Insulin Treatment in Patients with type 2 diabetes mellitus," *Ann. Int. Med.*, 134: 203-7 (2001).

Cheatham and Pfeutzner, "Desirable dynamics & performance of inhaled insulin compared to subcutaneous insulin given at mealtime in type 2 diabetes: A report from the technosphere/insulin study group" *Diabetes Technology & Therapeutics* 6:234-235 (2004).

Costello, et al., "Zinc inhibition of mitochondrial aconitase and its importance in citrate metabolism in prostate epithelial cells", *Journ. Biol. Chem.*, 272(46):28875-28881 (1997).

Dieter Köhler, "Aerosols for Systemic Treatment", *Lung (Suppl)*, 677-684 (1990).

Dunn, "Zinc-ligand interactions modulate assembly and stability of the insulin hexamer", *Biometals*, 18(4):295-303 (2005).

Edelman, "Type II Diabetes Mellitus," *Advances in Internal Medicine*, 43:449-500 (1998).(Abstract).

Elliott, et al., "Parenteral absorption of insulin from the lung in diabetic children," *Austr. Paediatr. J.* 23: 293-297 (1987).

(56) References Cited

OTHER PUBLICATIONS

Engelgau, et al., "Screening for tyoe 2 diabetes," *Diabetes Care* 1563(23):1-31 (2000).
Festa, et al., "LDL particle size in relation to insulin, proinsulin, and insulin sensitivity" *Diabetes Care* 22(10):1688-1693 (1999).
Garber, "Premixed insulin analogues for the treatment of diabetes mellitus", *Drugs*, 66(1):31-49 (2006).
Gupta, "Contemporary Approaches in Aerosolized Drug Delivery to the Lung," *J. Controlled Release*, 17(2): 127-147 (1991).
Haffner, et al., "Proinsulin and insulin concentrations I relation to carotid wall thickness" *Stroke* 29:1498-1503 (1998).
Hagedorn, et al., "Protamine insulin", *JAMA*, 106:177-180 (1936).
Hanley et al., "Cross-sectional and prospective associations between proinsulin and cardiovascular disease risk factors in a population experiencing rapid cultural transition" *Diabetes Care* 24(7):1240-1247 (2001).
Heubner, et al. Klinische Wochenschrift 16,2342 (1924).
Heyder, "Alveolar deposition of inhaled particles in humans," *Am. Ind. Hyg. Assoc. J.* 43(11): 864-866 (1982).
Heyder, *"Particle Transport onto Human Airway Surfaces" Eur. J. Respir. Dis. Suppl.* 119, 29-50 (1982).
Johnson, et al., "Turbuhaler®: a new device for dry powder terbutaline inhalation," *Allergy* 43(5):392-395 (1988).
Jones, et al., "An investigation of the pulmonary absorption of insulin in the rat", *Third European Congress of Biopharmaceutics and Pharmacokinetics*, 1987.
Katchalski, "Synthesis of Lysine Anhydride," *J. Amer. Chem. Soc.*, 68: 879-880 (1946).
Kohler, et al., "Pulmonary Administration . . . ," Abstract 298, *Diabetes* 33 (Suppl.):75A (1984).
Kohler, "Aerosols for Systemic Treatment", *Lung Suppl.* 677-683 (1990).
Komada, et al., "Intratracheal delivery of peptide and protein agents: absorption from solution and dry powder by rat lung," *J. Pharm. Sci.* 83(6): 863-867 (1994).
Kontny, et al."Issues Surrounding MDI Formulation Development with Non-CFC Propellants," *J. Aerosol Med.* 4(3), 181-187 (1991).
Kopple, "A Convenient Synthesis of 2,5-Piperazinediones," *J. Org. Chem.*, 33(2): 862-864 (1968).
Leahy, "Beta-cell dysfunction in type II diabetes mellitus," *Curr. Opin. Endocrinol. Diabetes* 2(4): 300-306 (1995).
Lee, et al., "Development of an Aerosol Dosage Form Containing Insulin," *J. Pharm. Sci.* 65(4), 567-572 (1976).
Lian, et al., "A self-complementary, self-assembling microsphere system: application for intravenous delivery of the antiepileptic and neuroprotectant compound felbamate," *J Pharm Sci* 89:867-875 (2000).
Lim, "Microencapsulation of Living Cells and Tissues," *J. Pharm. Sci.*, 70: 351-354 (1981).
Mathiowitz, "Morphology of Polyanhydride Microsphere Delivery Systems," *Scanning Microscopy*, 4: 329-340 (1990).
Mathiowitz, "Novel Microcapsules for Delivery Systems," *Reactive Polymers*, 6: 275-283 (1987).
Mathiowitz, "Polyanhydride Microspheres As Drug Carriers I. Hot-Melt Microencapsulation," *J. Controlled Release*, 5: 13-22 (1987).
Mathiowitz, "Polyanhydride Microspheres As Drug Carriers II. Microencapsulation by Solvent Removal," *J. Applied Poly. Sci.*, 35: 755-774 (1988).
Mathiowitz, "Polyanhydride Microspheres IV.Morpohology and Characterization of Systems Made by Spray Drying," *J. Applied Poly. Sci.*, 45: 125-134 (1992).
Moren, *Aerosols in Medicine*, (2nd ed.), Elsevier, pp. 321-350. 1993.
Nagai, et al., "Powder Dosage Form of Insulin for Nasal Administration," *J. Control Rel.*,1:15-22 (1984).

Okumura, et al., "Intratracheal delivery of insulin. Absorption from solution and aerosol by rat lung," *Int. J. Pharmaceuticals* 88: 63-73 (1992).
Patton & Platz, "Routes of Delivery: Case Studies. Pulmonary delivery of peptides and proteins for systemic action," *Adv. Drug. Del. Rev.* 8: 179-196 (1992).
Pfeiffer, "Insulin secretion in diabetes mellitus," *Am. J. Med.* 70(3): 579-88 (1981).
Pfutzner, et al., "Influence of small dose i.v., s.c. and pulmonary insulin treatment on prandial glucose control in patients with type 2 diabetes" 37th *Annual Meeting of the EASD, Glasgow*, Sep. 9-13, 2001 812 (2001) (abstract).
Polonsky, et al., "Abnormal patterns of insulin secretion in non-insulin-dependent diabetes mellitus," *N. England J. Med.* 318(19): 1231-39 (1988).
Prabhu, et al. "A study of factors controlling dissolution kinetic of zinc complexed protein suspensions in various ionic species", *Int. J. Pharm.*, 217(1-2):71-8 (2001).
Raskin, et al., "Continuous subcutaneous insulin infusion and multiple daily injection therapy are equally effective in type 2 diabetes" *Diabetes Care* 26:2598-2603 (2003).
Rosenstock, et al., "Reduced hypoglycemia risk with insulin glargine: a meta-analysis comparing insulin glargine with human NPH insulin in type 2 diabetes", Diabetes Care, 28(4):950-5 (2005).
Sakr, "A new approach for insulin delivery via the pulmonary route: design and pharmacokinetics in non-diabetic rabbits", *International Journal of Pharmaceutics*, 86:1-7 (1992).
Salib, "Utilization of Sodium Alginate in Drug Microencapsulation," *Pharazeutische Industrie*, 40(11a): 1230-1234 (1978).
Sawhney, "Bioerodible Hydrogels Based on Photopolymerized Poly-(ethylene glycol)-co-poly(a-hydroxy acid) Diacrylate Macromers," *Macromolecules*, 26: 581-587 (1993).
Schluter, et al., "Pulmonary Administration of Human Insulin in Volunteers and Type I Diabetics", *Diabetes*, 33 (Suppl.): 298 (1984).
Schneider, et al., "Stimulation by proinsulin of expression of plasminogen activator inhibitor type-I in endothelial cells" *Diabetes* 41(7):890-895 (1992).
Warren, et al., "Postprandial versus preprandial dosing of biphasic insulin aspart in elderly type 2 diabetes patients" *Diabetes Research and Clinical Practive* 66:23-29 (2004).
Waterhouse, et al. "Comparative assessment of a new breath-actuated inhaler in patients with reversible airways obstruction." *Respiration* 59:155-158 (1992).
Wigley, et al., "Insulin across respiratory mucosae by aerosol delivery," *Diabetes* 20(8): 552-556 (1971).
Witchert, "Low Molecular Weight PLA: A Suitable Polymer for Pulmonary Administered Microparticles," *J. Microencapsulation*, 10(2): 195-207 (1993).
Yoshida, et al., "Absorption of insulin delivered to rabbit trachea using aerosol dosage form," *J. Pharm. Sci.* 68(5): 670-671 (1979).
Zethelius, et al., "Proinsulin is an Independent Predictor of Coronary Heart Disease" *Circulation* 105:2153-2158 (2002).
Berge, et al. "Pharmacuetical Salts," *J. Pharmaceutical Sciences* 66(1):1-19 (1997).
Heinemann, et al. "Current Status of the development of inhaled insulin" *Br. J. Diabetes Vasc Dis* 4:295-301 (2004).
Steiner, et al. "Technosphere™/ Insulin- proof of concept study with new insulin formulation for pulmonary delivery" *Exp. Clin. Endocrinol. Diabetes* 110:17-21 (2002).
Kohler, et al. "Non-radioactive approach for measuring lung permeability: inhalation of insulin," *Atemw Lungebkrkh* 13:230-232 (1987). (Original in German and English Translation attached).
Raz, et al. "Pharmacodynamic and pharmacokinetics of dose ranging effects of oralin versus s.c. regular insulin in Type 1 diabetic patients," *Fourth Annual Diabetes Technology Meeting*, Philadelphia, PA, 2004.

Insulin Charge Distribution

- Cationic residues on insulin are clustered
- Multivalent anions may neutralize (mask) the charge

Figure 1

Epithelial Cells: Transwell setup

Figure 8 ial source
RAPID ACTING INJECTABLE INSULIN COMPOSITIONS

CROSS-REFERENCE TO RELATED APPLICATIONS

This application is a continuation of U.S. Ser. No. 11/869,693, filed Oct. 9, 2007, which is a continuation in part of U.S. Ser. No. 11/077,604 filed Mar. 11, 2005, which claims the benefit of and priority to U.S. Ser. No. 60/552,637, entitled "Sublingual Drug Delivery Compositions" to Roderike Pohl and Solomon S. Steiner filed Mar. 12, 2004, and U.S. Ser. No. 60/609,194, entitled "Sublingual Drug Delivery Compositions" to Roderike Pohl and Solomon S. Steiner filed Sep. 9, 2004.

FIELD OF THE INVENTION

The invention is in the general field of injectable rapid acting drug delivery insulin formulations.

BACKGROUND OF THE INVENTION

Diabetes Overview

Glucose is a simple sugar used by all the cells of the body to produce energy and support life. Humans need a minimum level of glucose in their blood at all times to stay alive. The primary manner in which the body produces blood glucose is through the digestion of food. When a person is not getting this glucose from food digestion, glucose is produced from stores in the tissue and released by the liver. The body's glucose levels are regulated by insulin. Insulin is a peptide hormone that is naturally secreted by the pancreas. Insulin helps glucose enter the body's cells to provide a vital source of energy.

When a healthy individual begins a meal, the pancreas releases a natural spike of insulin called the first-phase insulin release. In addition to providing sufficient insulin to process the glucose coming into the blood from digestion of the meal, the first-phase insulin release acts as a signal to the liver to stop making glucose while digestion of the meal is taking place. Because the liver is not producing glucose and there is sufficient additional insulin to process the glucose from digestion, the blood glucose levels of healthy individuals remain relatively constant and their blood glucose levels do not become too high.

Diabetes is a disease characterized by abnormally high levels of blood glucose and inadequate levels of insulin. There are two major types of diabetes—Type 1 and Type 2. In Type 1 diabetes, the body produces no insulin. In the early stages of Type 2 diabetes, although the pancreas does produce insulin, either the body does not produce the insulin at the right time or the body's cells ignore the insulin, a condition known as insulin resistance.

Even before any other symptoms are present, one of the first effects of Type 2 diabetes is the loss of the meal-induced first-phase insulin release. In the absence of the first-phase insulin release, the liver will not receive its signal to stop making glucose. As a result, the liver will continue to produce glucose at a time when the body begins to produce new glucose through the digestion of the meal. As a result, the blood glucose level of patients with diabetes goes too high after eating, a condition known as hyperglycemia. Hyperglycemia causes glucose to attach unnaturally to certain proteins in the blood, interfering with the proteins' ability to perform their normal function of maintaining the integrity of the small blood vessels. With hyperglycemia occurring after each meal, the tiny blood vessels eventually break down and leak. The long-term adverse effects of hyperglycemia include blindness, loss of kidney function, nerve damage and loss of sensation and poor circulation in the periphery, potentially requiring amputation of the extremities.

Between two and three hours after a meal, an untreated diabetic's blood glucose becomes so elevated that the pancreas receives a signal to secrete an inordinately large amount of insulin. In a patient with early Type 2 diabetes, the pancreas can still respond and secretes this large amount of insulin. However, this occurs at the time when digestion is almost over and blood glucose levels should begin to fall. This inordinately large amount of insulin has two detrimental effects. First, it puts an undue extreme demand on an already compromised pancreas, which may lead to its more rapid deterioration and eventually render the pancreas unable to produce insulin. Second, too much insulin after digestion leads to weight gain, which may further exacerbate the disease condition.

Current Treatments for Diabetes and their Limitations

Because patients with Type 1 diabetes produce no insulin, the primary treatment for Type 1 diabetes is daily intensive insulin therapy. The treatment of Type 2 diabetes typically starts with management of diet and exercise. Although helpful in the short-run, treatment through diet and exercise alone is not an effective long-term solution for the vast majority of patients with Type 2 diabetes. When diet and exercise are no longer sufficient, treatment commences with various non-insulin oral medications. These oral medications act by increasing the amount of insulin produced by the pancreas, by increasing the sensitivity of insulin-sensitive cells, by reducing the glucose output of the liver or by some combination of these mechanisms. These treatments are limited in their ability to manage the disease effectively and generally have significant side effects, such as weight gain and hypertension. Because of the limitations of non-insulin treatments, many patients with Type 2 diabetes deteriorate over time and eventually require insulin therapy to support their metabolism.

Insulin therapy has been used for more than 80 years to treat diabetes. This therapy usually involves administering several injections of insulin each day. These injections consist of administering a long-acting basal injection one or two times per day and an injection of a fast acting insulin at meal-time. Although this treatment regimen is accepted as effective, it has limitations. First, patients generally dislike injecting themselves with insulin due to the inconvenience and pain of needles. As a result, patients tend not to comply adequately with the prescribed treatment regimens and are often improperly medicated.

More importantly, even when properly administered, insulin injections do not replicate the natural time-action profile of insulin. In particular, the natural spike of the first-phase insulin release in a person without diabetes results in blood insulin levels rising within several minutes of the entry into the blood of glucose from a meal. By contrast, injected insulin enters the blood slowly, with peak insulin levels occurring within 80 to 100 minutes following the injection of regular human insulin.

A potential solution is the injection of insulin directly into the vein of diabetic patients immediately before eating a meal. In studies of intravenous injections of insulin, patients exhibited better control of their blood glucose for 3 to 6 hours following the meal. However, for a variety of medical reasons, intravenous injection of insulin before each meal is not a practical therapy.

One of the key improvements in insulin treatments was the introduction in the 1990s of rapid-acting insulin analogs, such as Humalog®, Novolog® and Apidra®. However, even with the rapid-acting insulin analogs, peak insulin levels typically occur within 50 to 70 minutes following the injection. Because the rapid-acting insulin analogs do not adequately mimic the first-phase insulin release, diabetics using insulin therapy continue to have inadequate levels of insulin present at the initiation of a meal and too much insulin present between meals. This lag in insulin delivery can result in hyperglycemia early after meal onset. Furthermore, the excessive insulin between meals may result in an abnormally low level of blood glucose known as hypoglycemia. Hypoglycemia can result in loss of mental acuity, confusion, increased heart rate, hunger, sweating and faintness. At very low glucose levels, hypoglycemia can result in loss of consciousness, coma and even death. According to the American Diabetes Association, or ADA, insulin-using diabetic patients have on average 1.2 serious hypoglycemic events per year, many of which events require hospital emergency room visits by the patients.

Because the time-course of insulin delivery to the blood plays such an important role in overall glucose control, there is significant need for insulin an injectable insulin that reaches the blood more rapidly than the rapid acting insulin analogs.

Therefore, it is an object of the invention to provide rapid acting injectable insulin compositions with improved stability and rapid onset of action.

SUMMARY OF THE INVENTION

Injectable insulin formulations with improved stability and rapid onset of action are described herein. The formulations may be for subcutaneous, intradermal or intramuscular administration. In the preferred embodiment, the formulations are administered via subcutaneous injection. The formulations contain insulin in combination with a chelator and dissolution agent, and optionally additional excipients. In the preferred embodiment, the formulation contains human insulin, a zinc chelator such as EDTA and a dissolution agent such as citric acid. These formulations are rapidly absorbed into the blood stream when administered by subcutaneous injection.

In the preferred embodiment, the insulin is provided as a dry powder in a sterile vial. This is mixed with a diluent containing a pharmaceutically acceptable carrier, such as water, a zinc chelator such as EDTA and a dissolution agent such as citric acid shortly before or at the time of administration. In another embodiment, the insulin is stored as a frozen mixture, ready for use upon thawing.

BRIEF DESCRIPTION OF THE DRAWINGS

FIGS. 3a and 3b are graphs comparing in vitro insulin transport (cumulative insulin in microunits) through oral epithelial cells in the transwell system of FIG. 2, with and without 0.45 mg EDTA/ml, as a function of acid selected as dissolution agent. EDTA was constant at 0.45 mg/mL while the acid concentrations were varied as follows: FIG. 3a, Aspartic acid (0.47 mg/mL), Glutamic acid (0.74 mg/mL), Succinic acid (0.41 mg/mL), Adipic acid (0.73 mg/mL) and Citric acid (0.29 mg/mL and 0.56 mg/mL), pH range 3.2-3.8. FIG. 3b, Maleic (0.32 mg/ml), Fumaric acid (1.28 mg/mL) and Oxalic acid (0.32 mg/mL), pH range 2-3. Two time periods (10 and 30 min.) were selected for comparative analysis. Results are mean plus or minus standard error measured, n=4.

DETAILED DESCRIPTION OF THE INVENTION

The insulin formulations of injectable human insulin described here are administered immediately prior to a meal or at the end of a meal. In the preferred embodiment, the formulation combines recombinant human insulin with specific ingredients generally regarded as safe by the FDA. The formulation is designed to be absorbed into the blood faster than the currently marketed rapid-acting insulin analogs. One of the key features of the formulation of insulin is that it allows the insulin to disassociate, or separate, from the six molecule, or hexameric, form of insulin to the single molecule, or monomeric, form of insulin and prevents re-association to the hexameric form. It is believed that by favoring the monomeric form, this formulation allows for more rapid delivery of insulin into the blood as the human body requires insulin to be in the form of a single molecule before it can be absorbed into the body to produce its desired biological effects. Most human insulin that is sold for injection is in the hexameric form. This makes it more difficult for the body to absorb, as the insulin hexamer must first disassociate to form dimers and then monomers.

I. Definitions

As used herein, "insulin" refers to human or non-human, recombinant, purified or synthetic insulin or insulin analogues, unless otherwise specified.

As used herein, "Human insulin" is the human peptide hormone secreted by the pancreas, whether isolated from a natural source or made by genetically altered microorganisms. As used herein, "non-human insulin" is the same as human insulin but from an animal source such as pig or cow.

As used herein, an insulin analogue is an altered insulin, different from the insulin secreted by the pancreas, but still available to the body for performing the same action as natural insulin. Through genetic engineering of the underlying DNA, the amino acid sequence of insulin can be changed to alter its ADME (absorption, distribution, metabolism, and excretion) characteristics. Examples include insulin lispro, insulin glargine, insulin aspart, insulin glulisine, insulin detemir. The insulin can also be modified chemically, for example, by acetylation. As used herein, human insulin analogues are altered human insulin which is able to perform the same action as human insulin.

As used herein, a "Chelator" or "chelating agent", refers to a chemical compound that has the ability to form one or more bonds to zinc ions. The bonds are typically ionic or coordination bonds. The chelator can be an inorganic or an organic compound. A chelate complex is a complex in which the metal ion is bound to two or more atoms of the chelating agent.

As used herein, a "solubilizing agent", is a compound that increases the solubility of materials in a solvent, for example, insulin in an aqueous solution. Examples of solubilizing agents include surfactants (TWEENS®); solvent, such as ethanol; micelle forming compounds, such as oxyethylene monostearate; and pH-modifying agents.

As used herein, a "dissolution agent" is an acid that, when added to insulin and EDTA, enhances the transport and absorption of insulin relative to HCl and EDTA at the same pH, as measured using the epithelial cell transwell plate assay described in the examples below. HCl is not a dissolution agent but may be a solubilizing agent. Citric acid is a dissolution agent when measured in this assay.

As used herein, an "excipient" is an inactive substance other than a chelator or dissolution agent, used as a carrier for the insulin or used to aid the process by which a product is manufactured. In such cases, the active substance is dissolved or mixed with an excipient.

II. Formulations

Formulations include insulin, a chelator and a dissolution agent(s) and, optionally, one or more other excipients. In the preferred embodiment, the formulations are suitable for subcutaneous administration and are rapidly absorbed into the fatty subcutaneous tissue. The choice of dissolution agent and chelator, the concentration of both the dissolution agent and the chelator, and the pH that the formulation is adjusted to, all have a profound effect on the efficacy of the system. While many combinations have efficacy, the preferred embodiment is chosen for many reasons, including safety, stability, regulatory profile, and performance.

In the preferred embodiment, at least one of the formulation ingredients is selected to mask any charges on the active agent. This may facilitate the transmembrane transport of the insulin and thereby increase both the onset of action and bioavailability for the insulin. The ingredients are also selected to form compositions that dissolve rapidly in aqueous medium. Preferably the insulin is absorbed and transported to the plasma quickly, resulting in a rapid onset of action (preferably beginning within about 5 minutes following administration and peaking at about 15-30 minutes following administration).

The chelator, such as EDTA, chelates the zinc in the insulin, thereby removing the zinc from the insulin solution. This causes the insulin to take on its dimeric and monomeric form and retards reassembly into the hexamer state. Since these two forms exist in a concentration-driven equilibrium, as the monomers are absorbed, more monomers are created. Thus, as insulin monomers are absorbed through the subcutaneous tissue, additional dimers dissemble to form more monomers. The monomeric form has a molecular weight that is less than one-sixth the molecular weight of the hexameric form, thereby markedly increasing both the speed and quantity of insulin absorption. To the extent that the chelator (such as EDTA) and/or dissolution agent (such as citric acid) hydrogen bond with the insulin, it is believed that it masks the charge on the insulin, facilitating its transmembrane transport and thereby increasing both the onset of action and bioavailability for insulin.

Insulin

The insulin can be recombinant or purified from a natural source. The insulin can be human or non-human. Human is preferred. In the most preferred embodiment, the insulin is human recombinant insulin. Recombinant human insulin is available from a number of sources. The insulin may also be an insulin analogue which may be based on the amino acid sequence of human insulin but having one or more amino acids differences, or a chemically modified insulin or insulin analog.

The dosages of the insulin depends on its bioavailability and the patient to be treated. Insulin is generally included in a dosage range of 1.5-100 IU, preferably 3-50 IU per human dose.

Dissolution Agents

Figure 1:
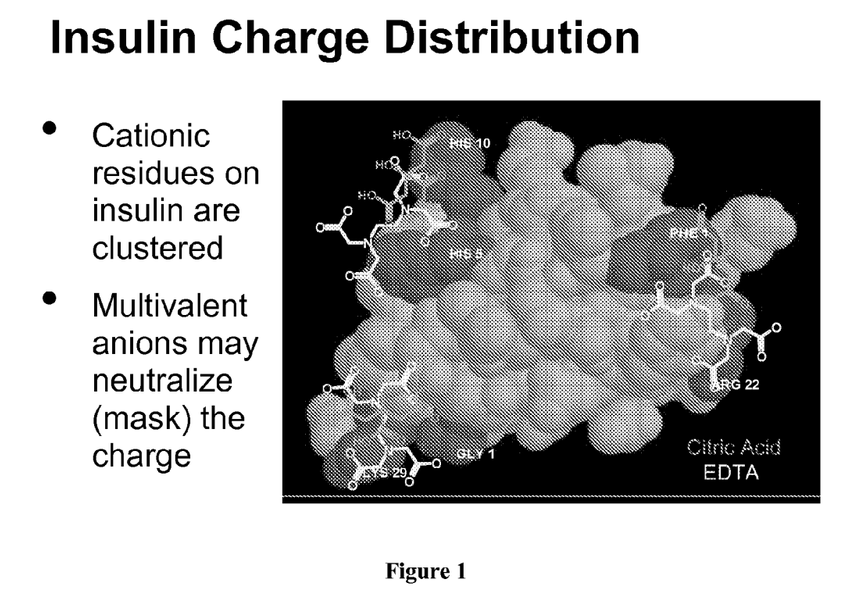
FIG. 1 is a three dimensional schematic of insulin showing exposed surface charges and overlaid with molecules ("dissolution and chelating agents") of appropriate size to mask the charge.

Certain acids appear to mask charges on the insulin, enhancing uptake and transport, as shown in FIG. 1. Those acids which are effective as dissolution agents include acetic acid, ascorbic acid, citric acid, glutamic, aspartic, succinic, fumaric, maleic, and adipic, relative to hydrochloric acid, as measured in the transwell assay described in the examples below. For example, if the active agent is insulin, a preferred dissolution agent is citric acid. The hydrochloric acid may be used for pH adjustment, in combination with any of the formulations, but is not a dissolution agent.

The range of dissolution agent corresponds to an effective amount of citric acid in combination with insulin and EDTA of between $9.37 \times 10^{-4}$ M to $9.37 \times 10^{-2}$ M citric acid.

Chelators

In the preferred embodiment, a zinc chelator is mixed with the active agent. The chelator may be ionic or non-ionic. Suitable chelators include ethylenediaminetetraacetic acid (EDTA), EGTA, alginic acid, alpha lipoic acid, dimercaptosuccinic acid (DMSA), CDTA (1,2-diaminocyclohexanetetraacetic acid), trisodium citrate (TSC). Hydrochloric acid is used in conjunction with TSC to adjust the pH, and in the process gives rise to the formation of citric acid, which is a dissolution agent.

In the preferred embodiment, the chelator is EDTA. For example, when the active agent is insulin, it is known that the chelator captures the zinc from the insulin, thereby favoring the dimeric form of the insulin over the hexameric form and facilitating absorption of the insulin by the tissues surrounding the site of administration (e.g. mucosa, or fatty tissue). In addition, the chelator hydrogen may bond to the active agent, thereby aiding the charge masking of the active agent and facilitating transmembrane transport of the active agent.

The range of chelator corresponds to an effective amount of EDTA in combination with insulin and citric acid of between $2.42 \times 10^{-4}$ M to $9.68 \times 10^{-2}$ M EDTA.

Excipients

Pharmaceutical compositions may be formulated in a conventional manner using one or more physiologically acceptable carriers comprising excipients and auxiliaries which facilitate processing of the active compounds into preparations which can be used pharmaceutically. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

In the preferred embodiment, one or more solubilizing agents are included with the insulin agent to promote rapid dissolution in aqueous media. Suitable solubilizing agents include wetting agents such as polysorbates, glycerin and poloxamers, non-ionic and ionic surfactants, food acids and bases (e.g. sodium bicarbonate), and alcohols, and buffer salts for pH control.

Stabilizers are used to inhibit or retard drug decomposition reactions which include, by way of example, oxidative reactions. A number of stabilizers may be used. Suitable stabilizers include polysaccharides, such as cellulose and cellulose derivatives, and simple alcohols, such as glycerol; bacteriostatic agents such as phenol, m-cresol and methylparaben; isotonic agents, such as sodium chloride, glycerol, and glucose; lecithins, such as example natural lecithins (e.g. egg yolk lecithin or soya bean lecithin) and synthetic or semisynthetic lecithins (e.g. dimyristoylphosphatidylcholine, dipalmitoylphosphatidylcholine or distearoyl-phosphatidylcholine; phosphatidic acids; phosphatidylethanolamines; phosphatidylserines such as distearoyl-phosphatidylserine, dipalmitoylphosphatidylserine and diarachidoylphospahtidylserine; phosphatidylglycerols; phosphatidylinositols; cardiolipins; sphingomyelins. In one example, the stabilizer may be a combination of glycerol, bacteriostatic agents and isotonic agents.

II. Methods of Making the Formulations

The injectable formulation contains insulin, a chelator, and a dissolution agent. In a preferred embodiment, the injectable formulation contains insulin, EDTA, Citric acid and saline and/or glycerol.

In the preferred embodiment, the subcutaneous injectable formulation is produced by mixing saline and/or glycerol, citric acid and EDTA to form a solution and sterilizing the solution (referred to as the "diluent"). The insulin is separately added to sterile water to form a solution, filtered, and a designated amount is placed into each of a number of separate sterile injection bottles. The insulin solution is lyophilized to form a powder and should be stored separately from the diluent to retain its stability. Prior to administration, the diluent is added to the insulin injection bottle. After the predetermined amount of insulin is subcutaneously injected into the patient, the remaining insulin solution may be stored, preferably by refrigeration.

In another embodiment, the insulin is combined with the diluent, sterile filtered into multi-use injection and frozen prior to use.

III. Methods of Using Formulations

The formulations may be subcutaneously administration or intramuscularly injection. The formulation is designed to be rapidly absorbed and transported to the plasma for systemic delivery.

Formulations containing insulin as the active agent may be administered to a type 1 or type 2 diabetic patient before or during a meal. Due to the rapid absorption, the compositions can shut off the conversion of glycogen to glucose in the liver, thereby preventing hyperglycemia, the main cause of complications from diabetes and the first symptom of type 2 diabetes. Currently available, standard, subcutaneous injections of human insulin must be administered about one half to one hour prior to eating to provide a less than desired effect, because the insulin is absorbed too slowly to shut off the production of glucose in the liver. Additionally, if given early enough in the progression of the disease, the subcutaneous insulin compositions may be able to slow or stop the progression of type 2 diabetes.

The present invention will be further understood by reference to the following non-limiting examples.

EXAMPLE 1

Figure 2:
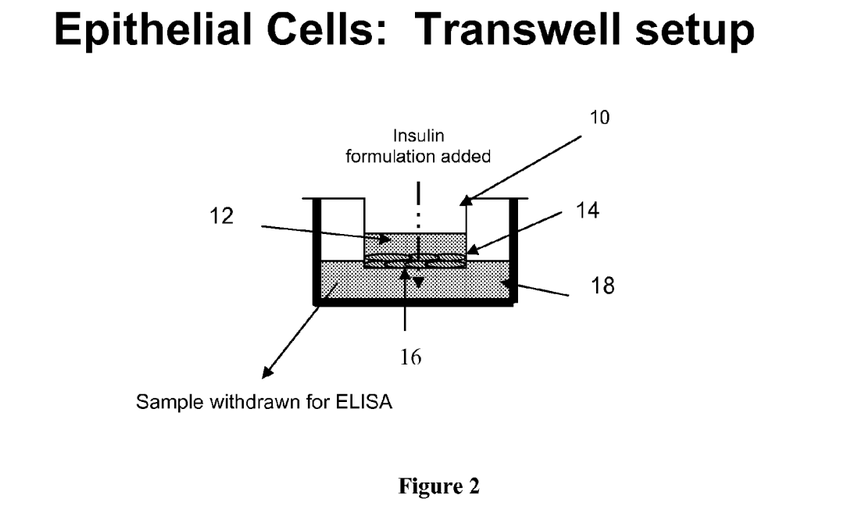
FIG. 2 is a schematic diagram of the transwell device 10 used to measure insulin absorption from a donor chamber 12 through 4-5 layers of immortalized oral epithelial cells 14 on a 0.1 micron filter 16 into a receiver chamber 18.

In Vitro Comparison of Uptake and Transport of Insulin Using Epithelial Cell Transwell Assay as a Function of Dissolution Agent Materials and Methods Oral epithelial cells were grown on transwell inserts for two weeks until multiple (4-5 layer) cell layers had formed, as shown in FIG. 2. The transport studies were conducted by adding the appropriate solutions to the donor well and removing samples from the receiver well after 10 minutes. Solutions consisted of water, +/−EDTA (0.45 mg/ml), NaCl (0.85% w/v), 1 mg/ml insulin and a sufficient amount of acid to maintain the pH at 3.8. Insulin amounts in the receiver wells were assayed using ELISA.

Results

Figure 3A:
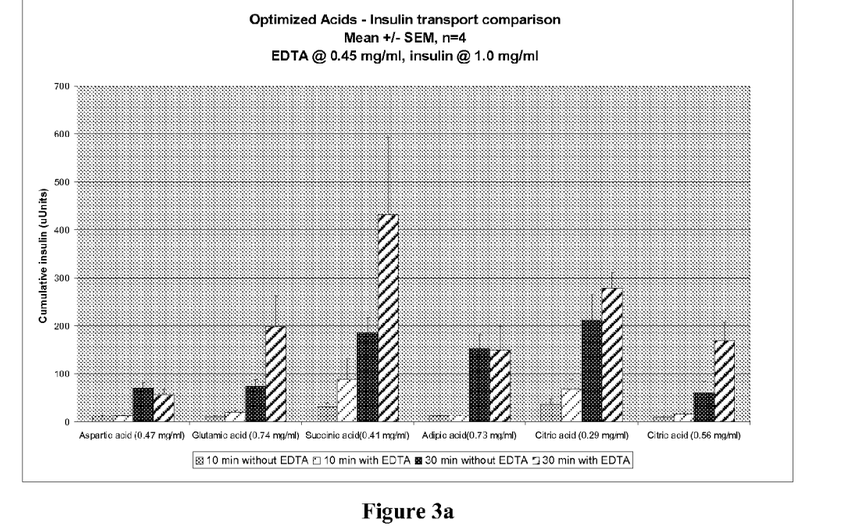
Figure 3B:
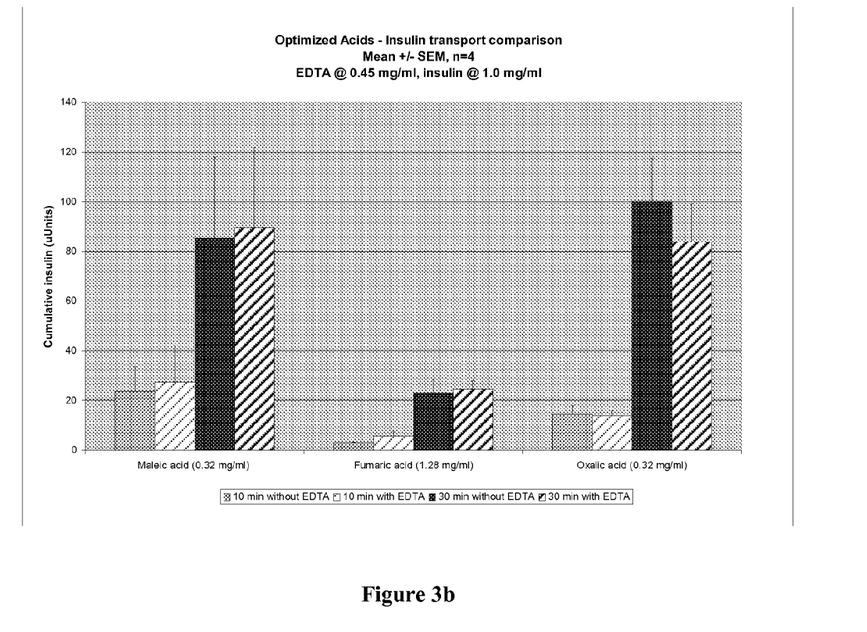

The results shown in FIGS. 3a and 3b demonstrate that some acids are more effective at enhancing uptake and transport of insulin through epithelial cells. These can be readily tested and compared to the results obtained using HCl, thereby providing a standard against which any acid can be tested and determined to be a dissolution agent (i.e., enhancing uptake and transport relative to HCl) or not.

Results obtained with acids with pH range of 3.2-3.8 are grouped in FIG. 3a. Stronger acids (pH<3) are grouped in FIG. 3b.

The results establish that the choice of acid with the same concentration of chelator has a substantial effect on the transport of insulin through cell culture. The preferred acid is citric acid.

EXAMPLE 2

In Vitro Comparison of Uptake and Transport of Insulin Using Epithelial Cell Transwell Assay as a Function of Concentration of Dissolution Agent Materials and Methods The materials and methods of Example 1 were used with different concentrations of reagents. In the study, equimolar concentrations of acid and chelator were added. Solutions consisted of water, +/−EDTA (0.56 mg/mL), NaCl (0.85% w/v), 1 mg/mL insulin and an acid: Aspartic acid (0.20 mg/mL), Glutamic acid (0.22 mg/mL) or citric acid (0.20 mg/ml). Citric acid was tested at a higher concentration of 1.8 mg/mL with and without chelator. This data is shown at two time periods, 10 and 30 minutes, post dosing of cell donor chambers.

Results

Figure 4A:
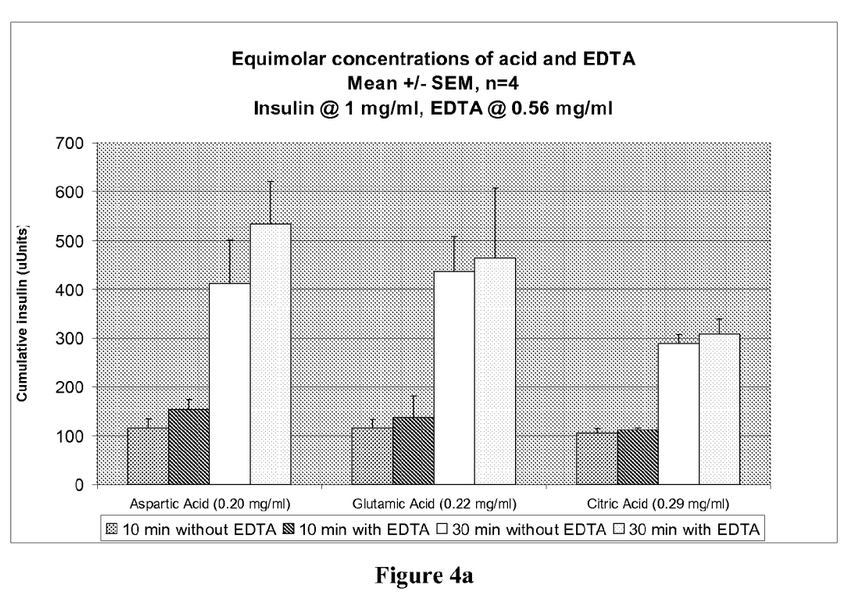
FIGS. 4a and 4b are graphs of in vitro insulin transport (cumulative insulin in microunits) through oral epithelial cells in the transwell system shown in FIG. 2, comparing different dissolution agents, with and without 0.56 mg EDTA/mL and acids at the following equimolar ($1.50 \times 10^{-3}$ Mol) concentrations: Aspartic acid (0.20 mg/mL), Glutamic acid (0.22 mg/mL) and citric acid (0.29 mg/ml) (FIG. 4a) and Citric acid at 1.80 mg/mL (FIG. 4b). Two time periods (10 and 30 min.) were selected for comparative analysis.

The results obtained with Aspartic acid (0.20 mg/mL), Glutamic acid (0.22 mg/mL) or citric acid (0.29 mg/ml) are shown in FIG. 4a. In this case, there was no significant difference seen with the addition of the chelator.

Figure 4B:
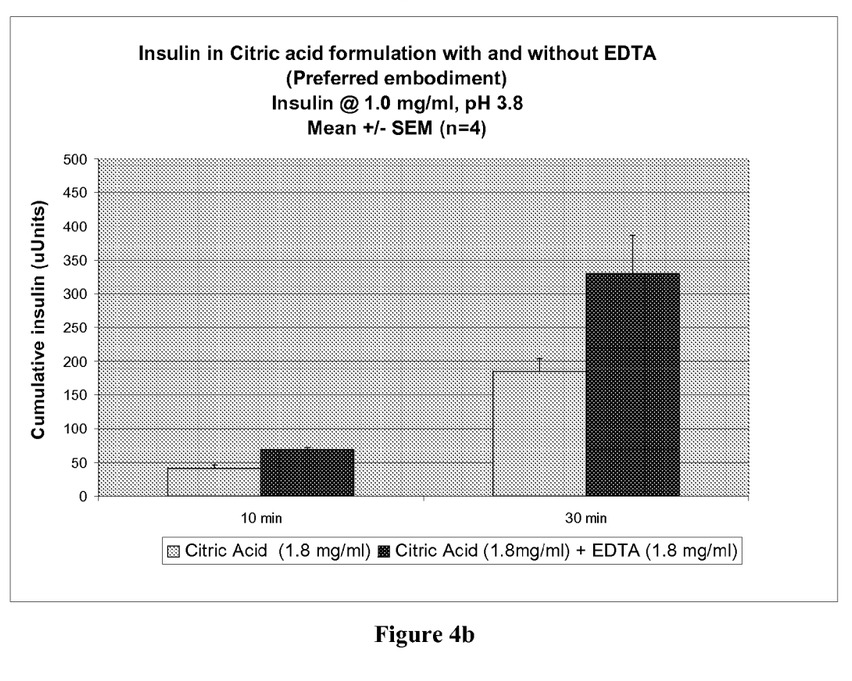

In contrast, the study using a higher concentration of Citric acid, at 1.80 mg/mL, does show a significant increase (t-test comparison, one sided) upon addition of the chelator to the solution. See FIG. 4b. This demonstrates that concentration of both components is important in optimizing uptake and transport.

EXAMPLE 3

In Vitro Comparison of Uptake and Transport of Insulin Using Epithelial Cell Transwell Assay as a Function of Chelator Materials and Methods Oral epithelial cells were grown on transwell inserts for two weeks until multiple (4-5 layer) cell layers had formed. The transport studies were conducted by adding the appropriate solutions to the donor well and removing samples from the receiver well after 10, 20 and 30 minutes.

The solutions were prepared immediately before the transwell experiments in the following way: Citric acid at 1.8 mg/ml was dissolved in 0.85% w/v saline and then one of the following chelators was added to this solution at the concentration shown: EDTA at 1.80 mg/ml, EGTA at 1.84 mg/ml, DMSA at 0.88 mg/ml and TSC at 1.42 mg/ml. Because CDTA was used in its liquid form, citric acid was added directly to the CDTA. In each of these cases, the concentration of chelator was constant at $4.84 \times 10^{-3}$ moles.

Insulin was then added at 1 mg/ml and the pH was re-adjusted to 3.8 if necessary. A control set of samples using only HCl for pH adjustment are included for comparison. At pH 3.8 alginic acid solidifies, and therefore, was not included for comparison in this example. Transwell experiments were done by adding 0.2 ml of each solution to the donor wells.

Insulin amounts in the receiver wells were assayed using ELISA.

Results

Figure 5:
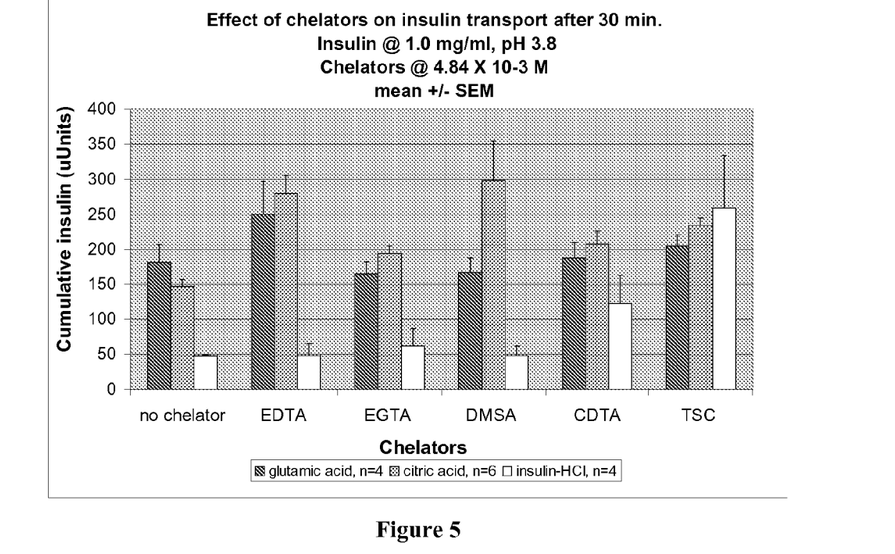
FIG. 5 is a graph of in vitro insulin transport through oral epithelial cells using the transwell system of FIG. 2 to compare efficacy of different chelators. Transport of insulin (1 mg/mL) from a solution containing glutamic acid, citric acid or HCl to which different chelators at the same molar concentration ($4.84 \times 10^{-3}$ Mol) were added through oral epithelial cells was measured (cumulative insulin, micromoles). The chelators were no chelator (control), EDTA, EGTA, DMSA, CDTA, and TSC.

A graph of 30 minute insulin data is shown in FIG. 5. There was significantly more insulin delivered through the cells when citric or glutamic acid was used, except as compared to results obtained with TSC (trisodium citrate). In the case of TSC, HCl was used for pH adjustment. The adjustment of pH generated citric acid, explaining these results.

As demonstrated by these results, enhancement of uptake and transport is dependent on the choice of chelator.

EXAMPLE 4

Preclinical Evaluation of Chelators in a Citric Acid Based Insulin Formulation in Swine Materials and Methods In concert with a published study, A. Plum, H. Agerso and L. Andersen. Pharmacokinetics of the rapid-acting insulin analog, insulin aspart, in rats, dogs, and pigs, and pharmacodynamics of insulin aspart in pigs. Drug Metab. Dispos., 28(2):155-60 (2000), it was determined that the elimination half life was a good determinant of the absorption of insulin, since a delay in the elimination implies slower absorption from the injection site. Therefore, a non-compartmental analysis of a small swine study was performed to examine PK and PD parameters, in particular elimination half life.

Diabetic swine were injected subcutaneously with one of four formulations of insulin. Three formulations contained a chelator (EDTA, EGTA or TSC) and fourth control contained only regular human insulin Humulin R®, no chelator. Citric acid (1.8 mg/ml) was used as the acid in all the chelator formulations, and NaCl and m-cresol were added for isotonicity and formulation sterility in all cases. The chelators were all at the same molar concentration of $4.84 \times 10^{-3}$ moles.

Swine were fasted overnight, and subcutaneously administered a dose of 0.125 U/kg human insulin containing EDTA (n=3) or 0.08 U/kg human insulin containing EGTA or TSC (n=2). Doses were reduced due to extreme blood glucose lowering with the higher dose. Blood glucose and insulin levels were determined at all timepoints, to 8 hours post dose.

Pharmacokinetic modeling was performed with WinNonlin, using a noncompartmental model with uniform weighting. Elimination half lifes were compared in Table 1:

TABLE 1

| Comparison of Blood Glucose in Swine as Function of Chelator | |
|---|---|
| Insulin | Half life "lamda z" (min. +/− sd) Terminal half life |
| Humulin/No chelator | 120 |
| Insulin/EDTA | 39.1 +/− 15.8 |
| Insulin/EGTA | 37.5 +/− 8.0 |
| Insulin/TSC | 30.1 +/− 9.0 |

The elimination half life of regular human insulin (120 min.) in this pilot study in swine was consistent with that seen in the literature and was used as a test point to validate the data. As this is considerably longer than following intravenous administration, this confirms there is continued slow absorption from the injection site following injection. The chelators in the citric acid formulation clearly show a reduction in this parameter, demonstrating that these three chelators are effective in enhancing the absorption of regular human insulin, although to different degrees.

EXAMPLE 5

Comparison of EDTA-Citric Acid Insulin Formulation to Regular Human Insulin in Human Clinical Trial Materials and Methods The aim of this study was to evaluate the pharmacodynamic (PD) properties of a test formulation containing insulin in combination with citric acid and EDTA, "CE". Five euglycemic glucose-clamps (Biostator; target blood glucose 90 mg/dl) were performed in 10 fasting healthy volunteers (mean age 40 (20-62 years range); BMI 22.5 (19.2-24.9) kg/m$^2$). Using a cross-over design with a fixed treatment order, 12 IU Regular insulin and 12 IU of CE insulin formulation were injected subcutaneously in the abdominal region.

Results

Figure 6:
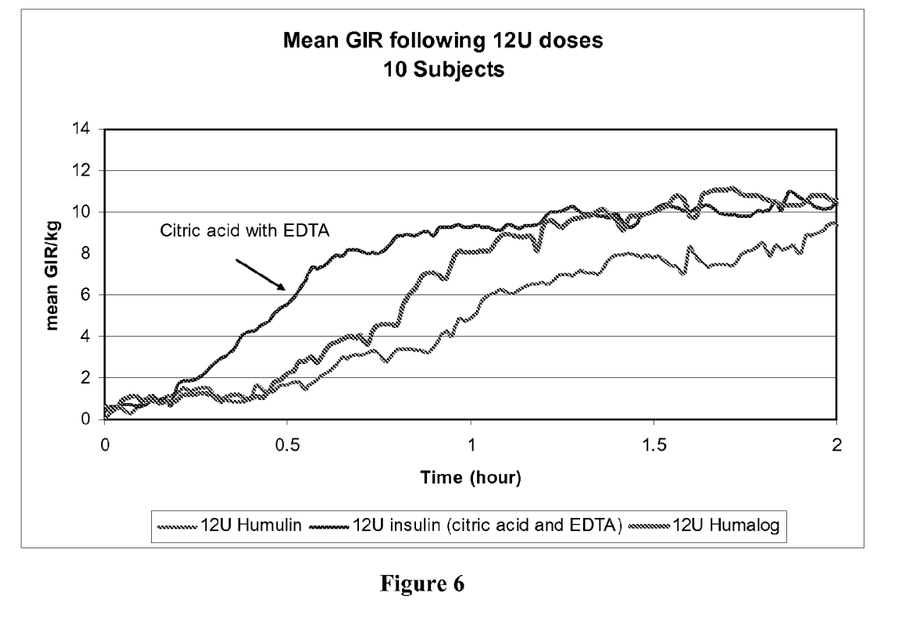
FIG. 6 is a graph of the in vivo pharmacodynamic effect of insulin prepared with citric acid and EDTA (12 U) in human subjects, compared to HUMALOG® (12 U) and HUMULIN R® (12 U), measures as mean GIR/kg.
Figure 7:
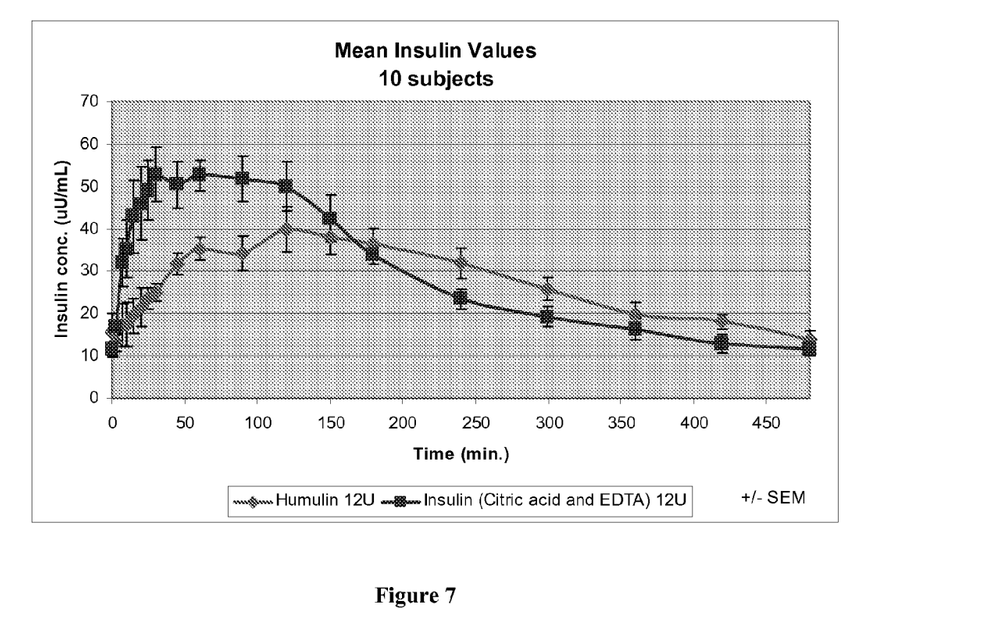
FIG. 7 is a graph of the in vivo pharmacokinetic effect of insulin prepared with citric acid and EDTA in humans, compared to HUMULIN R®, insulin concentration (microUnits/ml) over time (minutes). Mean values(±SEM, n=10) Insulin dose was 12 U/subject.

The results are shown in FIGS. 6 and 7. SC injection of CE resulted in a time-action profile that produced a significantly more rapid rise in glucose consumption regular human insulin (FIG. 6). The mean pharmacokinetic data confirm the PD results (FIG. 7).

This study shows that addition of citric acid and EDTA to regular human insulin improves the rate of absorption of insulin as demonstrated by a faster time to maximal concentration (FIG. 7) and a more rapid onset of action (FIG. 6) compared to regular human insulin alone.

EXAMPLE 6

Pharmacokinetics and Pharmacodynamics of CE Insulin,

Insulin Lispro and Regular Human Insulin When Injected Subcutaneously Immediately Before a Meal in Patients with Type 1 Diabetes Background and Aims:

The aim of this study was to determine the action of VIAject™ (a very rapid acting formulation of regular human insulin (RHI) combined with citric acid and EDTA, referred to above as CE), RHI, and insulin lispro (Lispro) on postprandial blood glucose (BG) excursions after a standard meal in patients with Type 1 diabetes.

Materials and Methods BG of 9 patients (5 males and 4 females; age 40±10 yrs, BMI 24.0±2.0 kg/m$^2$) were stabilized by means of a glucose clamp (target BG 120 mg/dl) prior to meal ingestion. The glucose infusion was turned off prior to the standard meal and insulin dosing. Using a cross-over study design with fixed treatment order, the same patient specific dose of VIAject™ (CE) Lispro or RHI was injected s.c. immediately before the meal. Subsequently, postprandial glucose excursions were continuously monitored for 8 hours and glucose infusion was re-initiated if BG<60 mg/dl. Plasma insulin levels were determined throughout the study.

Results

The results shown in Table 2 as the mean plus or minus standard deviation compare insulin Tmax after subcutaneous injection to type 2 diabetic patients after a meal, regular human insulin, insulin plus citric acid and EDTA (CE) and lispro. The results in Table 3 compare blood glucose for the same test subjects.

TABLE 2

Comparison of Insulin Tmax(min)

| Pharmacokinetics | RHI | Lispro | VIAject ™ (CE) |
|---|---|---|---|
| Ins Tmax (min) | 143 ± 29* | 62 ± 37 | 43 ± 36* |

*p < .001, paired t-test

TABLE 3

Comparison of Insulin Pharmacokinetics Blood Glucose

| Pharmacodynamics (0-180 min.) | RHI | Lispro | VIAject ™ (CE) |
|---|---|---|---|
| BG TMax (min.) | 93 ± 56* | 47 ± 28 | 41 ± 26* |
| BG Max (mg/dL) | 185 ± 44 | 158 ± 33 | 157 ± 27 |
| BG Min (mg/dL) | 103 ± 21 | 73 ± 31 | 87 ± 24 |
| BG Max-BG Min (mg/dL) | 82 ± 30 | 84 ± 11* | 70 ± 18* |

*p < 0.05, paired t-test

Figure 8:
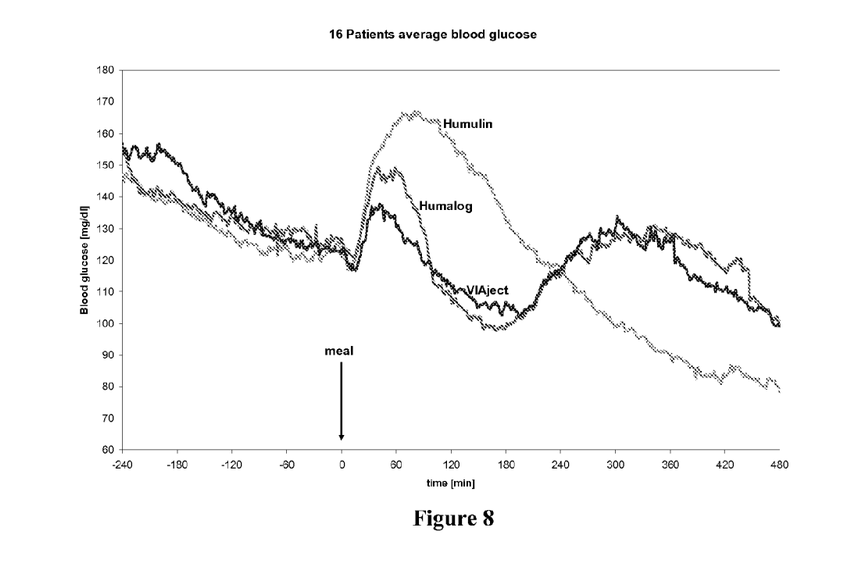
FIG. 8 is a graph of the in vivo pharmacodynamics of insulin prepared with citric acid and EDTA in 16 diabetic type 2 patients; compared to HUMULIN R® and HUMALOG®, plotting blood glucose (mg/dl) over time (minutes). The dosage used in the patient trial was patient specific, adjusted for each patient based on their current insulin therapy.

The total number of hypoglycemic events (hours requiring glucose infusion) 3 to 8 hours post injection were 13 with RHI, 11 with Lispro and 4 with the CE formulation. The mean total amount of glucose infused to prevent hypoglycemia during this time was six times higher for RHI and twice as much for Lispro than with VIAject™ (CE). The areas above and below the normal glycemic target zone (BG AUC above 140 and below 80 mg/dL) summed for all patients per group was 81,895 for RHI, 57,423 for Lispro and 38,740 mg/dL*min for VIAject™. The mean blood glucose levels are shown in FIG. 8.

In conclusion, VIAject™ (CE) was the fastest in reversing the rise in blood glucose following the standard meal. Patients treated with VIAject™ experienced reduced post prandial glucose excursions. In contrast, RHI had the highest glucose excursion, which is consistent with its slower absorption rate. Variability of the glucose levels (mean difference between maximal and minimal values) was significantly less for VIAject™ than Lispro, demonstrating VIAject's better glycemic control in these patients with Type 1 diabetes.

Modifications and variations of the present invention will be obvious to those skilled in the art from the foregoing description and are intended to come within the scope of the appended claims.

We claim:

1. An injectable insulin composition comprising an active agent and an effective amount of a dissolution agent and a zinc chelator to dissociate and charge mask the insulin to enhance uptake and transport of the insulin through epithelial cells as compared to insulin in combination with a zinc chelator and HCl,
    wherein the active agent consists of insulin hexamers dissociated by the zinc chelator,
    wherein the dissolution agent is selected from the group consisting of glutamic, succinic, aspartic, maleic, fumaric, and adipic acid, and
    wherein the zinc chelator is selected from the group consisting of ethylenediaminetetraacetic acid (EDTA), ethylene-bis(oxyethylene nitro) tetraacetic acid (EGTA), dimercaptosuccinic acid (DMSA), and CDTA (1,2-diaminocyclohexanetetraacetic acid), alone or in combination with ions of a metal.

2. The composition of claim 1, wherein the insulin is selected from the group consisting of human insulin and insulin analogs.

3. The composition of claim 2, wherein the insulin is human insulin.

4. An injectable insulin composition comprising an active agent and an effective amount of a dissolution agent and ethylenediaminetetraacetic acid (EDTA) to dissociate and charge mask the insulin to enhance uptake and transport of the insulin through epithelial cells as compared to insulin in combination with a zinc chelator and HCl,
    wherein the active agent consists of insulin hexamers dissociated by the zinc chelator and
    wherein the dissolution agent is selected from the group consisting of glutamic, succinic, aspartic, maleic, fumaric, and adipic acid.

5. The composition of claim 1 wherein the chelator is present in a concentration range corresponding to between $2.42 \times 10^{-4}$ M and $9.68 \times 10^{-2}$ M EDTA.

6. The composition of claim 1 wherein the dissolution agent is present in a concentration range corresponding to between $9.37 \times 10^{-4}$ M and $9.37 \times 10^{-2}$ M citric acid.

7. The composition of claim 4 wherein the EDTA is present in a concentration of between $2.42 \times 10^{-4}$ M and $9.68 \times 10^{-2}$ M EDTA and the dissolution agent is present in a concentration corresponding to between $9.37 \times 10^{-4}$ M and $9.37 \times 10^{-2}$ M citric acid.

8. The composition of claim 1 wherein the insulin is provided in a dry powder in a first container and at least one of the chelator and dissolution agent are provided in a second container containing a diluent.

9. The composition of claim 1 provided as a frozen pharmaceutically acceptable agent for treatment of a diabetic.

10. A method of treating a diabetic individual comprising injecting an effective amount of an injectable insulin composition comprising an active agent, an effective amount of a dissolution agent and a zinc chelator to dissociate and charge mask the insulin to enhance uptake and transport of the insulin through epithelial cells as compared to insulin in combination with a zinc chelator and HCl, wherein the active agent consists of insulin hexamers dissociated by the zinc chelator, and wherein the dissolution agent is selected from the group consisting of glutamic, succinic, aspartic, maleic, fumaric, and adipic acid.

11. The method of claim 10, wherein the chelator is selected from the group consisting of alginic acid, and alpha lipoic acid, alone or in combination with ions of a metal.

12. A method of treating a diabetic individual comprising injecting an effective amount of an injectable insulin composition comprising an active agent, an effective amount of a dissolution agent and a zinc chelator to dissociate and charge mask the insulin to enhance uptake and transport of the insulin through epithelial cells as compared to insulin in combination with a zinc chelator and HCl, wherein the active agent consists of insulin hexamers dissociated by the zinc chelator, wherein the dissolution agent is selected from the group consisting of glutamic, succinic, aspartic, maleic, fumaric, and adipic acid, and wherein the zinc chelator is selected from the group consisting of ethylenediaminetetraacetic acid (EDTA), ethylene-bis(oxyethylene nitro) tetraacetic acid (EGTA), trisodium citrate (TSC), dimercaptosuccinic acid (DMSA), CDTA (1,2-diaminocyclohexanetetraacetic acid) alone or in combination with ions of a metal.

13. The method of claim 12, wherein the chelator is EDTA.

14. The method of claim 10, wherein the chelator is selected from the group consisting of ethylene-bis(oxyethylene nitro) tetraacetic acid (EGTA), trisodium citrate (TSC), dimercaptosuccinic acid (DMSA), CDTA (1,2-diaminocyclohexanetetraacetic acid) alone or in combination with ions of a metal.

* * * * *